United States Patent [19]
Vanney et al.

[11] Patent Number: 6,113,630
[45] Date of Patent: Sep. 5, 2000

[54] TRANSMYOCARDIAL IMPLANT WITH MINIMIZED CORONARY INSERTION

[75] Inventors: Guy P. Vanney, Blaine; Robert E. Kohler, Oakdale, both of Minn.

[73] Assignee: Heartstent Corporation, St. Paul, Minn.

[21] Appl. No.: 09/373,790

[22] Filed: Aug. 13, 1999

[51] Int. Cl.$^7$ ..................................................... A61F 2/04
[52] U.S. Cl. .............................. 623/1.37; 623/1.1; 623/12
[58] Field of Search ..................................... 623/1.1, 1.24, 623/1.37, 12

[56] References Cited

U.S. PATENT DOCUMENTS

| | | |
|---|---|---|
| 5,287,861 | 2/1994 | Wilk . |
| 5,409,019 | 4/1995 | Wilk . |
| 5,429,144 | 7/1995 | Wilk . |
| 5,755,682 | 5/1998 | Knudson et al. . |
| 5,830,222 | 11/1998 | Makower . |

FOREIGN PATENT DOCUMENTS

| | | |
|---|---|---|
| WO 98/06356 | 2/1998 | WIPO . |
| WO 98/08456 | 3/1998 | WIPO . |
| WO 98/46115 | 10/1998 | WIPO . |
| WO 99/17683 | 4/1999 | WIPO . |

OTHER PUBLICATIONS

U.S. application No. 08/944,313, filed Oct. 6, 1997.
U.S. application No. 09/063,160, filed Apr. 20, 1998.

*Primary Examiner*—David J Isabella
*Attorney, Agent, or Firm*—Merchant & Gould P.C.

[57] ABSTRACT

A transmyocardial implant establishes a blood flow path through a myocardium between a heart chamber and a lumen of a coronary vessel residing on an exterior of the heart. The implant includes a coronary portion sized to be received with the vessel. A myocardial portion is sized to pass through the myocardium into the heart chamber. A transition portion connecting the coronary and myocardial portion for directing blood flow from the myocardial portion and into the coronary portion. The transition portion is an arcuate bend and at least a portion of the arcuate bend terminates at the vessel opening at a point of tangency of the arcuate bend.

8 Claims, 1 Drawing Sheet

TRANSMYOCARDIAL IMPLANT WITH MINIMIZED CORONARY INSERTION

BACKGROUND OF THE INVENTION

1. Field of the Invention

This invention pertains to an implant for passing blood flow directly between a chamber of the heart and a coronary vessel. More particularly, this invention pertains to such an implant with an enhanced design for avoiding damage to the coronary vessel.

2. Description of the Prior Art

Commonly assigned U.S. Pat. No. 5,755,682 and co-pending and commonly assigned U.S. patent application Ser. No. 08/882,397 filed Jun. 25, 1997 (also filed as international application Ser. No. PCT/US97/13980 published as PCT WO 98/06356) teach an implant for defining a blood flow conduit directly from a chamber of the heart to a lumen of a coronary vessel. An embodiment disclosed in the aforementioned application teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced patent application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997 (filed internationally as PCT Ser. No. PCT/US98/17310 published as WO 99/17683) entitled "Transmyocardial Implant" teaches an implant such as that shown in the aforementioned '682 patent and '397 application with an enhanced fixation structure. One embodiment of the enhanced fixation structure includes a fabric surrounding at least a portion of the conduit to facilitate tissue growth on the exterior of the implant.

Implants such as those shown in the aforementioned patent applications include a portion to be placed within a coronary vessel and a portion to be placed within the myocardium. When placing a portion of the implant in the coronary artery or other coronary vessel, the artery is incised by an amount sufficient to insert the implant. Preferably, the artery is ligated distal to an obstruction. A transverse incision is made through the artery distal to the ligation. Tools and procedures for such an implantation are shown and described in commonly assigned and copending U.S. patent application Ser. No. 09/063,160 filed Apr. 20, 1998 (filed internationally as PCT/US99/08343).

In the foregoing references, a constantly open blood flow path is preferred. However, the references also teach a conduit with a valve which closes during diastole. The afore-mentioned PCT/US97/13980 teaches a conduit with a valve which only partially closes during diastole to permit a washing back-flow.

Conduits which include a valve or which otherwise close during the heart cycle are shown in U.S. Pat. Nos. 5,287,861; 5,409,019 and 5,429,144 (all to Wilk). Conduits are also shown in PCT International Publication Nos. WO 98/08456 and WO 98/46115. The alleged benefits of a valve in such a conduit are described in Kashem et al., "Feasibility Study of Left Ventricle to Coronary Artery Perfusion for Severe Coronary Artery Diseases", ASAIO Journal, Vol. 45, No. 2 (March-April, 1999) (Abstract).

Transmyocardial implants are placed in a dynamic environment. The heart is constantly beating. It is desirable to avoid or reduce relative movement between the implant and the coronary vessel. Such relative movement may otherwise result in a tissue response which could partially or fully occlude the vessel or implant. Also, L-shaped implants may be difficult to align with the coronary vessel. Misalignment may impede blood flow. It is an object of the present invention to address such issue.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart. The implant includes a coronary portion sized to be received with the vessel. A myocardial portion is sized to pass through the myocardium into the heart chamber. A transition portion connecting the coronary and myocardial portion for directing blood flow from the myocardial portion and into the coronary portion. The transition portion is an arcuate bend and at least a portion of the arcuate bend terminates at the vessel opening at a point of tangency of the arcuate bend.

DESCRIPTION OF THE PREFERRED EMBODIMENT

Figure 1:
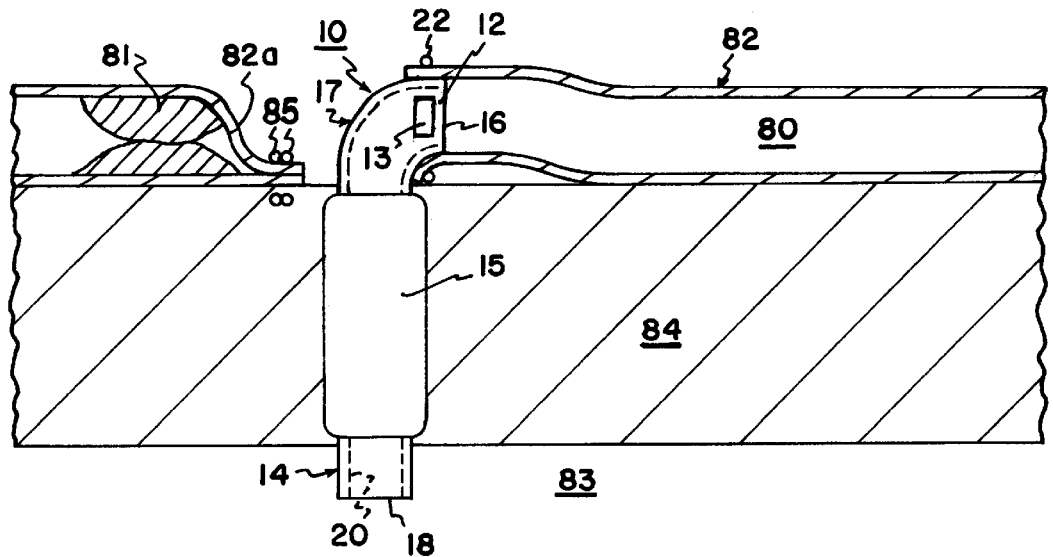
FIG. 1 is a side-elevation view of a transmyocardial implant according to the present invention shown in place defining a blood flow path from a left ventricle to a coronary artery.

With initial reference to FIG. 1, a conduit 10 is shown in the form of an L-shaped tube. The conduit 10 is preferably formed of titanium but may be other biocompatible material. The material of the conduit 10 is preferably radially rigid in order to withstand contraction forces of the myocardium. By way of non-limiting example, the conduit 10 will have an outside diameter of about 2.5 millimeters and an internal diameter of about 2.0 millimeters to provide a wall thickness of about 0.5 millimeters. As will be more fully described, the size of the conduit 10 is sized to match a vessel. Coronary arteries requiring bypass typically have diameters ranging from 4.0 mm to 1.0 mm and the appropriately sized conduit 10 is selected to match the vessel.

Figure 4:
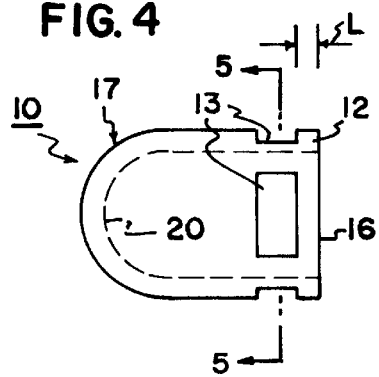
FIG. 4 is a top plan view of the implant of FIG. 1.
Figure 5:
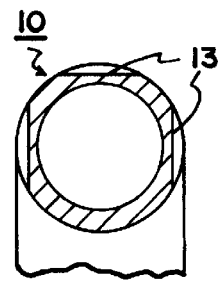
FIG. 5 is a cross-sectional view taken along section line 5—5 of FIG. 4.

The tube 10 has a vessel portion 12 sized to be received within the lumen of a coronary vessel such as the lumen 80 of a coronary artery 82 distal to an obstruction 81 as illustrated in FIG. 1. The coronary portion 12 has a coronary opening 16 to discharge blood axially into the vessel lumen 80 along a discharge axis X—X (shown in FIG. 2). A plurality of flats 13 (shown best in FIGS. 4 and 5) are formed around the vessel portion 12 spaced a distance L from the coronary opening 16.

The conduit 10 has a myocardial portion 14 extending at a right angle to the discharge axis X—X. The myocardial portion 14 is sized to extend from the coronary artery 82 directly through the myocardium 84 and protrude into the left ventricle 83 of a patient's heart.

A fabric cuff 15 surrounds the myocardial portion 14. The cuff 15 permits integration of the myocardium 84.

The myocardial portion 14 has a myocardial opening 18 in communication with an interior 20 of the implant 10. Therefore, blood can freely flow through the implant 10 between the left ventricle 83 and the lumen 80 of the coronary artery 82. Blood flows out of discharge opening 16 at the discharge axis X—X parallel with the axis of lumen 80.

The longitudinal axis X—X of the discharge opening 16 is aligned with the axis of the lumen 80. A suture 22 surrounds the artery 82 over the flats 13 to secure the artery 82 to the coronary portion 12. The proximal portion 82a of the coronary artery is ligated by sutures 85. A surgical procedure for placing a conduit 10 and tools for such procedure are more fully described in commonly assigned and co-pending U.S. patent application Ser. No. 09/063,160 filed Apr. 20, 1998. Preferably, the patient will be on an anti-platelet drug therapy such as aspirin, triclopidine, clopidogrel or GPIIbIIIa antagonists (so-called "super aspirins").

The conduit 10 is sized to be inserted into the lumen 80 without undue dilation of the artery 82. While damage to endothelial cells is unavoidable, it is desired to avoid damage to the structural architecture of the artery 82 (e.g., to avoid damage the internal elastic lamina of the artery 82). As will become apparent, by avoiding undue dilation of the artery 82, the artery 82 is free to expand in response to blood pressure within the artery 82 and define an annular space between the artery 82 and the conduit 10 distal to the stay suture 22. Also, avoidance of undue dilation avoids hyperplastic response of a damaged artery.

To avoid undue dilation, the diameter of the artery 82 (on a beating heart) is sized. The internal diameter can be measured through angiography, ultrasonography or other method. Alternatively (but less desirable), the artery internal diameter can be approximated by measuring the outside diameter of the artery 82 and assuming a wall thickness (e.g., about 0.5 mm).

With the predetermined artery internal diameter, the conduit 10 is selected for the outside diameter of the conduit 10 to not over-dilate the artery 82 as described above. Preferably, the conduit 10 is sized so that after implantation, the artery 82 is not so dilated that it cannot further expand in response to blood pressure. To insure such remaining flexibility, the conduit 10 is preferably sized to have a diameter the same as or less than the internal diameter of the artery 82. With the given example, a 2.5 mm outside diameter implant 10 is used in a 2.5 mm to 3.0 mm artery. For larger arteries, a larger conduit 10 is used. Preferably, the artery inside diameter is no more than 0.5 mm to 1.0 mm larger than the outside diameter of the conduit 10. While the upper limit of 1.0 mm is not necessary to practice the invention, selecting too small of a conduit 10 unnecessarily restricts the amount of blood which can flow through the conduit 10 into the artery 82.

Figure 2:
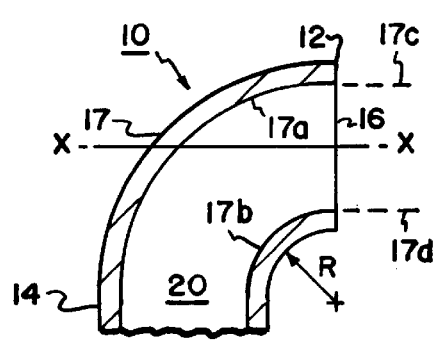
FIG. 2 is an enlarged cross-sectional view of a transition portion and vessel portion of the implant of FIG. 1.

The coronary and myocardial portions 12, 14 are joined by a transition portion 17 in a 90° C. bend between portions 12, 14. As shown in cross-section, the 90° C. bend results in upper and lower arcuate surfaces 17a, 17b connecting the myocardial portion 14 to the discharge opening 16. With reference to FIG. 2, the transition portion has a radius R of 2.25 mm to 3.21 mm.

The present invention is directed to a minimized length of the coronary portion 12. So minimized, an edge of the discharge opening 16 is positioned at a point of parallel tangency of at least one of the upper and lower surfaces 17a, 17b. By "point of parallel tangency" it is meant that point on the arcuate surface 17a, 17b where the tangent of the surface is first parallel to the discharge axis X—X. The upper tangent line is numbered 17c and the lower tangent line is numbered 17d.

Figure 3:
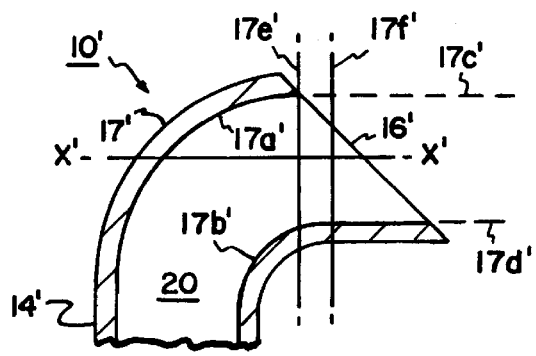
FIG. 3 is the view of FIG. 2 showing an alternative embodiment of the implant of FIG. 2.

In FIG. 2, the opening 16 passes through the point of parallel tangency of both the upper and lower surfaces 17a, 17b. In the embodiment of FIG. 3, elements in common with those of FIG. 2 are numbered identically with the addition of an apostrophe to distinguish the embodiment. All such elements are the same as those of FIG. 2 except the opening 16' is non-perpendicular to axis X'—X'. As a result, only the upper edge of opening 16' passes through a point of parallel tangency (i.e., passes through the point of parallel tangency of the upper surface 17a'). The lower edge of the opening 16' is distal to the point of parallel tangency of lower surface 17b '). Lines 17e', 17f are perpendicular to the tangency lines 17c', 17d', respectively, at the point of parallel tangency. As shown in FIG. 3, opening 16' intersects line 17c' at line 17e' but intersects line 17d' distal to line 17f. In FIG. 2, opening 16 intersects each of lines 17c, 17d at the upper and lower points of parallel tangency.

With the structure of FIG. 2, only the minimum amount of material is placed within the artery 82 while maintaining a structure to provide laminar flow of blood into the lumen 80 parallel with axis X—X. This minimizes the amount of foreign material-to-natural tissue contact. This minimizes the amount of surface area over which there could be differential movement and micro-wear between the artery 82 and the implant 10.

The minimized coronary insertion of the present invention also contributes to enhanced volumetric blood flow in the event the implant 10 is placed with the discharge axis X—X offset from the axis of the lumen 80. This can occur by reason of rotation of the implant about the longitudinal axis of the myocardial portion 14 resulting in the opening being partially pointed toward a side of the artery. In the event of a long coronary portion 12, such an angular offset results in a reduced portion of the area of the opening 16 facing distally in the lumen. By minimizing the length of the coronary portion 12, the amount of such area reduction is minimized for any given angular offset.

In the embodiment of FIG. 3, the protruding lower surface 17b' results in an extending portion which assists in stabilizing the implant 10.

An additional advantage of the present invention is a reduced size implant 10 more suitably adapted for use in minimally invasive surgical techniques.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto.

What is claimed is:

1. A transmyocardial implant for defining a blood flow pathway directly from a left ventricle to a coronary vessel, the implant comprising:

a hollow conduit having a myocardial opening and a vessel opening; said hollow conduit comprising:

a myocardial portion sized to pass through the myocardium into the left ventricle when said myocardial portion is positioned in the left ventricle;

a vessel portion sized to be received within the coronary vessel, said vessel portion having a discharge axis for substantially axial discharge through said vessel opening into the coronary vessel; and a transition portion connecting said vessel portion and said myocardial portion for directing blood flow from said myocardial portion into said vessel portion, said transition portion being an arcuate bend having a radius, the radius defining a line perpendicular to the discharge axis, at least a part of said vessel portion terminating at the line perpendicular to the discharge axis.

2. An implant according to claim 1 further comprising a suture guide on said vessel portion.

3. An implant according to claim 1 wherein said vessel opening is in a plane perpendicular to the discharge axis.

4. An implant according to claim 1 wherein a part of said myocardial portion extends into the left ventricle.

5. An implant according to claim 1 further comprising a cuff extending between said myocardial portion and said vessel portion.

6. A transmyocardial implant for defining a blood flow pathway directly from a left ventricle to a coronary vessel, the implant comprising:

a hollow conduit having a myocardial opening and a vessel opening; said conduit comprising:

a myocardial portion sized to pass through the myocardium into the left ventricle when the myocardial portion is positioned in the left ventricle;

a vessel portion sized to be received within the coronary vessel and with said vessel opening of the conduit having a discharge axis for substantially axial discharge into the vessel;

a transition portion connecting said vessel portion and said myocardial portion for directing blood flow from the myocardial portion and into the vessel portion, said transition portion being an arcuate bend;

said arcuate bend having a point of tangency at which a tangent line of said arcuate bend is substantially parallel to said discharge axis, at least a portion of said vessel portion terminating at the point of tangency of the arcuate bend.

7. An implant according to claim 6 wherein said arcuate bend terminates at the vessel opening at a point of tangency of the arcuate bend.

8. An implant according to claim 6 wherein an edge of said conduit at said vessel opening closest to said myocardial portion extends beyond said point of tangency.

* * * * *